United States Patent [19]

Irikura et al.

[11] Patent Number: 4,578,392

[45] Date of Patent: Mar. 25, 1986

[54] PYRAZOLO[1,5-A]PYRIDINE DERIVATIVES AND ANTI-ALLERGIC COMPOSITIONS CONTAINING THEM

[75] Inventors: Tsutomu Irikura, Tokyo; Keigo Nishino, Oomiya; Seigo Suzue, Kuki; Toshiya Ikeda, Oomiya, all of Japan

[73] Assignee: Kyorin Pharmaceutical Co., Ltd., Tokyo, Japan

[21] Appl. No.: 586,928

[22] Filed: Mar. 7, 1984

[30] Foreign Application Priority Data

Mar. 14, 1983 [JP] Japan ................................. 58-41958

[51] Int. Cl.[4] ..................... A61K 31/44; C07D 471/04
[52] U.S. Cl. ..................................... 514/300; 546/121
[58] Field of Search ........................ 546/121; 514/300

[56] References Cited

U.S. PATENT DOCUMENTS 4,028,370 6/1977 Irikura ................................. 260/296
4,097,483 6/1978 Irikura ................................. 260/296

OTHER PUBLICATIONS

K. T. Potts, U. P. Singh, and J. Bhattacharyya, The J. of Organic Chemistry, vol. 33, Oct. 1968, pp. 3766–3770.
Robert Morrison and Robert Boyd, "Organic Chemistry", 2nd Ed., Allyn and Bacon, Inc., Boston (1966).

Primary Examiner—Henry R. Jiles
Assistant Examiner—Bernard I. Dentz
Attorney, Agent, or Firm—Armstrong, Nikaido, Marmelstein & Kubovcik

[57] ABSTRACT

The present invention is concerned with certain novel pyrozolo[1,5-a]pyridine derivatives, which are prepared by various means. The compounds of the present invention are antiallergic agents, referred to as SRS-A antagonists, and useful for treatment of allergic diseases.

3 Claims, No Drawings

PYRAZOLO[1,5-A]PYRIDINE DERIVATIVES AND ANTI-ALLERGIC COMPOSITIONS CONTAINING THEM

DETAILED DESCRIPTION OF THE INVENTION

The present invention is concerned with certain novel pyrazolo[1,5-a]pyridine derivatives, which are useful for treating allergic diseases, with process for their preparations, and with compositions containing them.

It is known that chemical mediators are released from certain cells such as mast cells in response to antigen-antibody reaction and induce allergic disorders. The mediators, histamine and SRS-A (slow reacting substance of anaphylaxis), involved in immediate allergic reactions are of importance to medicinal chemists and the SRS-A is particulary noted in allergic asthma. Accordingly, most major companies have attempted to develop allergic mediator release inhibitors and/or antagonists against the mediators for treatment of allergic diseases. Consequently, antihistaminics such as diphenhydramine and chlorpheniramine, and mediator release inhibitors such as disodium cromoglycate are on the market.

But antihistaminics have not been proved to be effective in bronchial asthma and disodium cromoglycate must be insufflated as a powder owing to its orally inactive property.

Thus no agent satisfying clinical requirements is clearly visible at this time.

It is very important therefore to develop an orally active and more potent drug, referred to as SRS-A release inhibitors and antagonists of SRS-A.

As a result of the investigation, the present inventors have now unexpectedly found that new derivatives of pyrazolo[1,5-a]pyridine possess a potent antiallergic activity, especially potent antagonistic activity against SRS-A. This is unobvious from the known arts of the similar series.

Thus, the present compounds constitute valuable agents which are used in human and veterinary medicine for the treatment of systemic or localized allergic diseases such as bronchial asthma, allergic rhinitis, urticaria and so on.

According to the present invention, therfore, there are provided novel pyrazolo[1,5-a]pyridine derivatives of the formula [I],

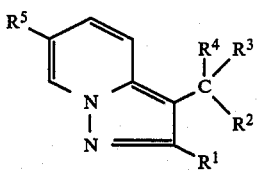

[I]

in which $R^1$ is a straight or branched alkyl radical having 1 to 6 carbon atoms, $R^2$ is a hydrogen or straight, branched or cyclic alkyl radical having 1 to 6 carbon atoms, $R^3$ is a hydrogen, straight or branched alkyl having 1 to 6 carbon atoms, or allyl radical, $R^4$ is a hydrogen, —$OR^6$ (in which $R^6$ is a hydrogen, alkyl having 1 to 5 carbon atoms, which alkyl may optionally be substituted by one or two hydroxy radicals, allyl or 2,3-epoxypropyl radical) or, together with $R^2$ or $R^3$ forms

(in which $R^7$ and $R^8$ are each independently a hydrogen or alkyl having 1 to 5 carbon atoms), and $R^5$ is a hydrogen, methyl or methoxy radical. These compounds can not be presumed either structurally or pharmacologically from the prior arts.

The compounds are used in intact or in pharmaceutical compositions, which additionally comprise an inert physiologically acceptable carrier.

For oral or parenteral administration, suitable forms of pharmaceutical composition are, for example, compressed tablets, capsules, liquores, injections, inhalations, ointments, suppositories and so on.

The present invention also comprises a process for the preparation of the present compounds. The compounds can be prepared by either of the following (1) to (7).

(1) When $R^3$ is a hydrogen and $R^4$ is a hydroxy radical in the formula [I], the compound has the formula [III],

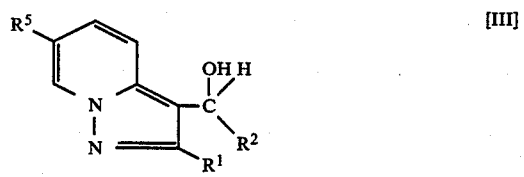

[III]

in which $R^1$, $R^2$ and $R^5$ have the above-stated meanings, and can be prepared by treating a compound of the formula [II],

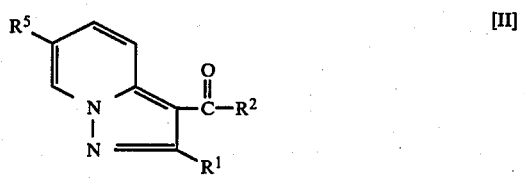

[II]

in which $R^1$, $R^2$ and $R^5$ have the above-stated meanings, with a reducing agent such as sodium borohydride and so on. The reaction is preferably carried out by mixing the two reactants in a suitable solvent such as water, methanol, ethanol, a mixture of them and so on.

(2) When $R^4$ is a hydroxy radical and $R^3$ is other than a hydrogen in the formula [I], the compound has the formula [V]:

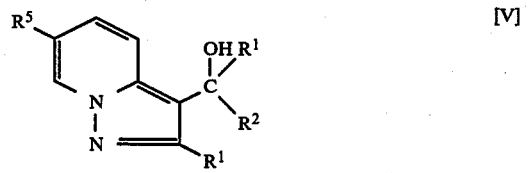

[V]

in which $R^1$, $R^2$ and $R^5$ have the above-stated meanings and $R^9$ is a straight or branched alkyl having 1 to 6 carbon atoms or allyl radical and can be prepared by treating the compoud [II] with a Grignard reagent of the formula [IV], XMg—R$^9$ [IV]

in which R$^9$ have the above-stated meanings and X is a chlorine, bromin or iodine atom. The condensation reaction is carried out by adding the compound [II] to the Grignard reagent [IV] prepared by usual method in a suitable solvent such as dry ether or dry teterahydrofuran at room, cooled or elevated temperature.

(3) When R$^4$ is —OR$^6$ (in which R$^6$ is other than a hydrogen) in the formula [I], the compound has the formula [VIII],

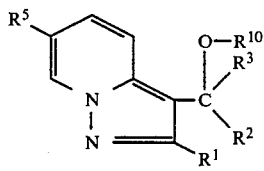
[VIII]

in which R$^1$, R$^2$, R$^3$ and R$^5$ have the above-stated meanings and R$^{10}$ has the same meaning as R$^6$ but for a hydrogen in the formula [I], and can be prepared by condensing a compound of the formula [VII],

Z—R$^{10}$ [VII]

in which R$^{10}$ has the above-stated meanings and Z is a halogen or arylsulfonyloxy radical, with a compound of the formual [VI],

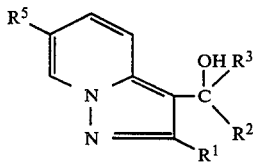
[VI]

in which R$^1$, R$^2$, R$^3$ and R$^5$ have the above-stated meanings.

The reaction of [VI] and [VII] is preferably carried out in the presence of an acceptor for acid which is formed in the reaction. The acid acceptors may be either an inorganic or organic acceptor such as an alkali metal carbonate or a tertiary amine.

It is also convenient for the condensation that the compound [VI] is at first converted to its metal alcoholate by treating with, e.g., powder sodium of sodium hydride in a suitable solvent such as dimehtylformamide or teterahydrofuran and then the alcoholate is reacted with the alkylating agent [VII].

(4) When R$^4$ is a propoxy radical and R$^3$ is other than an allyl radical in the formula [I], the compound can be prepared by catalytic reduction of the allyl derivative of the formula [IX],

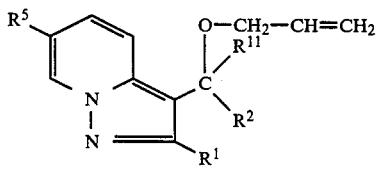
[IX]

in which R$^1$, R$^2$ and R$^5$ have the above-stated meanings and R$^{11}$ is a hydrogen or straight or branched alkyl radical having 1 to 6 carbon atoms, at atmospheric pressure and room temperature. The catalyst used in this reaction may be palladium-on-charcoal and so on.

(5) The compound of the formula [X],

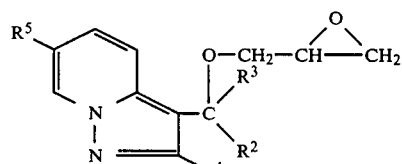
[X]

in which R$^1$, R$^2$, R$^3$ and R$^5$ have the above-stated meanings, which was prepared by the procedure described herein above, can be converted to the corresponding 2-hydroxypropoxy derivative by the treatment with lithium aluminum hydride in a suitable solvent such as dry ether or dry tetrahydrofuran.

(6) When R$^4$ together with R$^2$ or R$^3$ forms

in the formula [I], the compound is represented by the formula [XI],

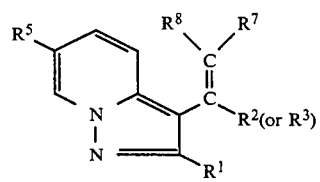
[XI]

in which R$^1$, R$^2$, R$^3$, R$^5$, R$^7$ and R$^8$ have the above-stated meanings, and can be prepared by dehydrating the compound [VI] by treating with a dehydrating agent such as acetic anhydride or potassium hydrogen sulfate at elevated temperature.

(7) The compound [XI] obtained herein above, can be converted to a compound of the formula [XII],

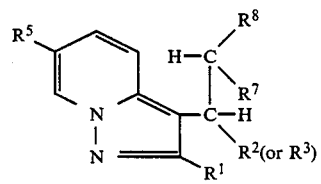
[XII]

in which R$^1$, R$^2$, R$^3$, R$^5$, R$^7$ and R$^8$ have the above-stated meanings, by catalytic reduction at atmospheric pressure and room temperature in a solvent such as methanol or ethanol. The catalyst used in this reaction may be palladium-on-charcoal.

A certain class of the compounds of the present invention has one or more asymmetric carbons and aliphatic double bond. Therefore, the present invention also comprises the compounds of optical or geometrical isomers.

In order that the invention may be more fully understood, the following examples are given by way of illustration.

REFERENCE EXAMPLE

2-Isopropyl-6-methoxypyrazolo[1,5-a]pyridine

To a solution of 50 g of 2-isopropylpyrazolo[1,5-a]pyridine in 300 ml of chloroform were added about 20 ml of bromine until the solution became faintly yellow under stirring and cooling to 5°–15° C. After the addition was completed, the mixture was stirred at room temperature for 30 minutes, then poured into aqueous 10% sodium bisulfite solution and extracted with chloroform. The chloroform layer was washed with aqueous 10% sodium hydroxide and then water, dried over anhydrous sodium sulfate, and concentrated in vacuo to give 75 g of crude 2-isopropyl-3-bromopyrazolo[1,5-a]pyridine, as colorless needles, mp 51°–52° C.

To a solution of this bromide in 300 ml of chloroform were slowly added 50 ml of bromine. The mixture was heated to reflux for 2.5 hours. After cooling, the reaction mixture was treated with the same manner described above to give crude product which was purified by silica gel column chromatography, eluting with hexane-benzene (1:1). Forty-five grams of 2-isopropyl-3,6-dibromopyrazolo[1,5-a]pyridine were obtined as fine crystals, mp 54°–55° C.

To sodium methylate prepared from 65 ml of methanol and 7 g of sodium were added 0.5 g of cuprous iodide and a solution of 10 g of the above-obtained dibromide in 12 ml of dimethylformamide. The mixture was heated at reflux temperature for 4 hours, and then poured into water. The mixture was extracted with chloroform. The chloroform layer was dried over anhydrous sodium sulfate and concentrated in vacuo. The oily residue was chromatographed on a column of silica gel, eluting with dichloromethane-ethyl acetate (10:1). The first fraction gave 4 g of 2-isopropyl-3-bromo-6-methoxypyrazolo[1,5-a]pyridine as an oil and the second afforded 1.6 g of oily 2-isopropyl-6-methoxypyrazolo[1,5-a]pyridine.

A solution of the above-obtained 3-bromo-6-methoxy derivative in 100 ml of ethanol was agitated in a hydrogen atmosphere at atmospheric pressure and room temperature in the presence of 1 g of 10% palladium-on-charcoal. After absorption ceased, the solution was filtered and concentrated to dryness. The residue was applied to column chromatography of silica gel, eluting with dichloromethane to yield 2.7 g of 2-isopropyl-6-methoxy derivative wich was identical with the above-obtained product. Total yield of the desired product from 2-isopropyl-3,6-dibromo derivative was 4.3 g (51%).

EXAMPLE 1

2-Isopropyl-3-cyclopentylcarbonylpyrazolo[1,5-a]pyridine

A mixture of 5 g of 2-isopropylpyrazolo[1,5-a]pyridine and 5 ml of cyclopentylcarbonyl chloride was heated at 160° C. for 4.5 hours and, after cooling, poured into aqueous potassium hydroxide solution. The mixture was extracted with dichloromethane and the organic layer was dried over anhydrous sodium sulfate, concentrated to dryness. The residue was applied to a column of silica gel, eluting with ethyl acetate-hexane(1:9), to give 2.1 g of the title compound as colorless crystals, mp 106°–110° C.

Analysis (%) for $C_{16}H_{20}N_2O$: Calcd. (Found); C, 74.96 (75.06); H, 7.86 (7.83); N, 10.93 (10.94).

Using the procedure described in Example 1, other new compounds have been obtained, and their physical constants are indicated in Table 1.

TABLE 1

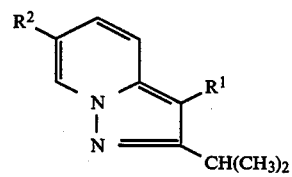

| Example No. | R¹ | R² | M.P. (°C.) | Yield (%) | Anal. (%) Calcd. Found C | H | N |
|---|---|---|---|---|---|---|---|
| 2 | CO cyclo C₄H₇ | H | 97.5–98.5 | 50 | 74.35 74.54 | 7.48 7.52 | 11.56 11.57 |
| 3 | COCH₂CH₂CH₃ | H | 84–85 | 53 | 73.01 73.22 | 7.88 7.91 | 12.16 12.15 |
| 4 | COCH(CH₃)₂ | CH₃O | oil | 46 | 69.20 68.95 | 7.74 7.68 | 10.76 10.72 |

EXAMPLE 5

2-Isopropyl-3-(1-hydroxy-2-methylpropyl)-pyrazolo[1,5-a]pyridine

To a solution of 25% of 2-isopropyl-3-isobutyrylpyrazolo[1,5-a]pyridine in 500 ml of methanol were added in small portions 20 g of sodium borohydride under stirring and cooling. After 30 minutes at room temperature, the mixture was refluxed for 2.5 hours and then concentrated by dryness. Water was added to the residue and the mixture was extracted with dichloromethane. The organic layer was washed with saturated brine, dried over anhydrous sodium sulfate and concentrated in vacuo. To the oily residue were added 2 ml of water to give the colorless crystalline monohydrate, mp 73° C., weighing 21.3 g (78%).

Analysis (%) for $C_{14}H_{20}N_2O \cdot H_2O$: Calcd. (Found); C, 67.17 (67.30); H, 8.85 (8.64); N, 11.19 (11.15).

Using the procedure described in Example 5, other new compounds have been obtained, and their physical constants are summarized in Table 2.

TABLE 2

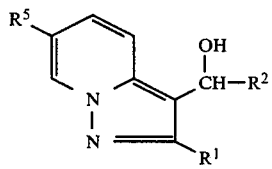

| Example No. | $R^1$ | $R^2$ | $R^5$ | M.P. (°C.) | Yield (%) | Anal. (%) Calcd. Found C | H | N |
|---|---|---|---|---|---|---|---|---|
| 6 | —CH(CH$_3$)$_2$ | -cycloC$_5$H$_9$ | H(H$_2$O) | 85 | 77 | 69.53 | 8.75 | 10.14 |
|   |   |   |   |   |   | 69.19 | 8.44 | 10.05 |
| 7 | —CH(CH$_3$)$_2$ | -cycloC$_4$H$_7$ | H(⅓.H$_2$O) | 85–86 | 94 | 70.28 | 8.39 | 10.93 |
|   |   |   |   |   |   | 70.51 | 8.36 | 10.84 |
| 8 | —CH(CH$_3$)$_2$ | —CH$_2$CH$_3$ | H | oil | 20 | 71.52 | 8.31 | 12.83 |
|   |   |   |   |   |   | 71.62 | 8.28 | 12.53 |
| 9 | —CH(CH$_3$)$_2$ | —CH$_2$CH$_2$CH$_3$ | H | 73–77 | 17 | 72.38 | 8.67 | 12.06 |
|   |   |   |   |   |   | 72.36 | 8.73 | 12.00 |
| 10 | —CH$_3$ | —CH(CH$_3$)$_2$ | H | oil | 83 | 70.56 | 7.89 | 13.71 |
|   |   |   |   |   |   | 70.02 | 8.13 | 13.11 |
| 11 | —CH$_2$CH$_2$CH$_3$ | —CH$_2$CH$_2$CH$_3$ | H | 79–80 | 99 | 72.38 | 8.67 | 12.06 |
|   |   |   |   |   |   | 72.53 | 8.75 | 11.97 |
| 12 | —CH(CH$_3$)$_2$ | —CH(CH$_3$)$_2$ | —CH$_3$ | 101–102 | 54 | 73.13 | 9.00 | 11.37 |
|   |   |   |   |   |   | 73.20 | 9.04 | 11.34 |
| 13 | —CH(CH$_3$)$_2$ | —CH(CH$_3$)$_2$ | —OCH$_3$ | 127–130 | 77 | 68.67 | 8.45 | 10.68 |
|   |   |   |   |   |   | 68.87 | 8.45 | 10.69 |

EXAMPLE 14

2-Isopropyl-3-(1-hydroxy-2,2-dimethylpropyl)-pyrazolo[1,5-a]pyridine

To a suspension of 1.6 g of magnesium in 10 ml of dry ether was added a solution of 9.3 g of tert. butylbromide in 15 ml of dry ether under stirring. After the addition was completed, the stirring was continued for an hour at room temperature. To the Grignard reagent were added 2.5 g of 2-isopropyl-3-formylpyrazolo[1,5-a]pyridine in 5 ml of dry benzene under stirring. The mixture was stirred for an hour at room temperature and 11 hours at reflux temperature. The reaction mixture was treated with 100 ml of aqueous 20% ammonium chloride solution and extracted with ether. The ether layer was washed with saturated brine, dried over anhydrous sodium sulfate and concentrated in vacuo. The residue was subjected to silica gel column chromatography, eluted with dichloromethane, to give 1.7 g (52%) of pale yellow crystals, mp 95° C.

Analysis (%) for C$_{15}$H$_{22}$N$_2$O.2/3H$_2$O: Calcd. (Found); C, 69.73 (69.65); H, 9.10 (9.15); N, 10.84 (10.79).

EXAMPLE 15

2-Isopropyl-3-(1-hydroxy-1-ethyl-2-methylpropyl)-pyrazolo[1,5-a]pyridine

To a suspension of 1.32 g of magnesium in 10 ml of dry ether was gradually added a solution of 17 g of ethyl iodide in 15 ml of dry ether with stirring. After the addition was completed, the stirring was continued for an hour at room temperature. To the mixture was gradually added a solution of 2.5 g of 2-isopropyl-3-isobutyrylpyrazolo[1,5-a]pyridine in 10 ml of dry benzene under stirring. The mixture was stirred for an hour at room temperature, treated with 150 ml of aqueous 20% ammonium chloride solution under ice cooling, and extracted with ether. The ether layer was washed with saturated brine, dried over anhydrous sodium sulfate and cencentrated to dryness. The residue was recrystallized from hexane to give 1.5 g (54%) of the desired derivative as pale gray prisms, mp 96°–98° C.

Analysis (%) for C$_{16}$H$_{24}$N$_2$O: Calcd. (Found); C, 73.80 (73.88); H, 9.29 (9.44); N, 10.76 (10.78).

Using the procedure described in Example 15, other new compounds have been obtained, and these physical constants are shown in Table 3.

TABLE 3

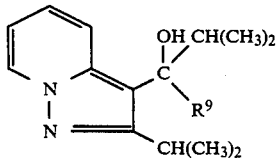

| Example No. | $R^9$ | M.P. (°C.) | Yield (%) | Anal. (%) Calcd. Found C | H | N |
|---|---|---|---|---|---|---|
| 16 | —CH$_3$(3/2.H$_2$O) | 69 | 4 | 65.90 | 9.22 | 10.25 |
|   |   |   |   | 66.09 | 8.68 | 10.12 |
| 17 | —CH$_2$CH$_2$CH$_3$ | 111–113 | 81 | 74.41 | 9.55 | 10.21 |
|   |   |   |   | 74.59 | 9.52 | 10.21 |

TABLE 3-continued

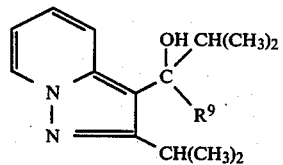

| Example No. | $R^9$ | M.P. (°C.) | Yield (%) | Anal. (%) Calcd. Found C | H | N |
|---|---|---|---|---|---|---|
| 18 | —CH$_2$CH$_2$CH$_2$CH$_3$ | 100–102 | 78 | 74.96 | 9.79 | 9.71 |
|  |  |  |  | 75.02 | 9.71 | 9.68 |
| 19 | —CH$_2$CH$_2$CH$_2$CH$_2$CH$_2$CH$_3$ | 73.5–74.5 | 55 | 75.90 | 10.19 | 8.85 |
|  |  |  |  | 75.98 | 10.19 | 8.87 |
| 20 | —CH$_2$CH=CH$_2$ | 62–64 | 34 | 74.96 | 8.88 | 10.28 |
|  |  |  |  | 75.15 | 8.98 | 10.29 |

EXAMPLE 21

2-Isopropyl-3-(1-methoxy-2-methylpropyl)-pyrazolo[1,5-a]pyridine

To a suspension of 1.24 g of sodium hydride (55% oil suspension) in 20 ml of tetrahydrofuran was slowly added a solution of 3 g of 2-isopropyl-3-(1-hydroxy-2-methylpropyl)pyrazolo[1,5-a]pyridine in 5 ml of dry tetrahydrofuran under stirring and cooling. After the addition was completed, the stirring was continued for 5 minutes at room temperature, then reflux temperature for 15 minutes. The mixture was cooled with ice-water, to which 5.5 g of methyl iodide were added, and stirred for an hour at room temperature. After treating with aqueous 20% ammonium chloride solution, the mixture was extracted with ether. The ether layer was washed with saturated brine, dried over anhydrous sodium sulfate and concentrated to dryness. The residue was applied to silica gel column chromatography, eluted with ethyl acetate-benzene (1:4) to give 2.8 g (88%) of the desired product as pale yellow oil.

Analysis (%) for $C_{15}H_{22}N_2O$: Calcd. (Found); C, 73.13 (73.26); H, 9.00 (9.05); N, 11.37 (11.16).

Using the procedure described in Example 21, other new compounds have been obtained, and these physical constants are enumerated in Table 4.

TABLE 4

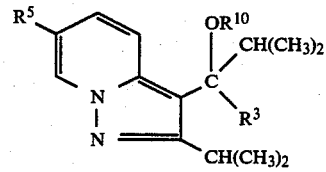

| Example No. | $R^3$ | $R^{10}$ | $R^5$ | mp | Yield (%) | Anal. (%) Calcd. Found C | H | N |
|---|---|---|---|---|---|---|---|---|
| 22 | H | —CH$_2$CH$_3$ | H | oil | 85 | 73.80 | 9.29 | 10.76 |
|  |  |  |  |  |  | 73.47 | 9.34 | 10.69 |
| 23 | H | —CH$_2$CH=CH$_2$ | H | oil | 85 | 74.96 | 8.88 | 10.28 |
|  |  |  |  |  |  | 74.74 | 8.80 | 10.04 |
| 24 | H | —CH$_2$CH$_2$CH$_3$ | H | oil | 42 | 74.41 | 9.55 | 10.21 |
|  |  |  |  |  |  | 74.58 | 9.49 | 10.16 |
| 25 | H | —CH$_2$CH$_2$CH$_2$CH$_3$ | H | oil | 70 | 74.96 | 9.78 | 9.71 |
|  |  |  |  |  |  | 75.04 | 9.77 | 9.61 |
| 26 | H | —CH$_3$ | —CH$_3$ | oil | 75 | 73.80 | 9.29 | 10.76 |
|  |  |  |  |  |  | 73.50 | 9.25 | 10.75 |
| 27 | H | —CH$_2$CH=CH$_2$ | —CH$_3$ | oil | 61 | 75.48 | 9.15 | 9.78 |
|  |  |  |  |  |  | 75.16 | 9.19 | 9.61 |
| 28 | H | —CH$_3$ | —OCH$_3$ | oil | 79 | 69.53 | 8.75 | 10.14 |
|  |  |  |  |  |  | 69.24 | 8.73 | 10.09 |
| 29 | H | —CH$_2$CH=CH$_2$ | —OCH$_3$ | oil | 73 | 71.49 | 8.67 | 9.26 |
|  |  |  |  |  |  | 71.03 | 8.71 | 9.19 |
| 30 | —CH$_2$CH$_3$ | —CH$_3$ | H | oil | 87 | 74.41 | 9.55 | 10.21 |
|  |  |  |  |  |  | 74.56 | 9.57 | 10.20 |
| 31 | —CH$_2$CH$_3$ | —CH$_2$CH=CH$_2$ | H | oil | 69 | 75.96 | 9.39 | 9.32 |
|  |  |  |  |  |  | 75.88 | 9.45 | 9.18 |
| 32 | —C$_3$H$_7$ | —CH$_2$CH=CH$_2$ | H | oil | 94 | 76.39 | 9.61 | 8.91 |
|  |  |  |  |  |  | 76.54 | 9.73 | 8.87 |
| 33 | —C$_4$H$_9$ | —CH$_2$CH=CH$_2$ | H | oil | 48 | 76.78 | 9.82 | 8.53 |
|  |  |  |  |  |  | 76.93 | 9.88 | 8.51 |

TABLE 4-continued

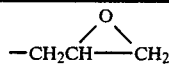

| Example No. | $R^3$ | $R^{10}$ | $R^5$ | mp | Yield (%) | Anal. (%) Calcd. Found C | H | N |
|---|---|---|---|---|---|---|---|---|
| 34 | —H | —CH$_2$CH$\underset{\diagdown\!O\!\diagup}{\qquad}$CH$_2$ | H | oil | 44 | 70.80 70.40 | 8.39 8.44 | 9.71 9.61 |

EXAMPLE 35

2-Isopropyl-3-(1-ethyl-1-propoxy-2-methylpropyl)-pyrazolo[1,5-a]pyridine

A solution of 500 ml of 2-isopropyl-3-(1-allyloxy-1-ethyl-2-methylpropyl)pyrazolo[1,5-a]pyridine (Example 31) in 20 ml of ethanol was stirred in a hydrogen atmosphere at atmospheric pressure and room temperature in the presence of 20 mg of 10% palladium-on-charcoal. Absorption ceased after an hour. The solution was filtered and concentrated to dryness in vacuo. The residue was applied to silica gel column chromatography, eluted with dichloromethane, to give 350 mg (70%) of the desired compound as pale yellow oil.

Analysis (%) for $C_{19}H_{30}N_2O$: Calcd. (Found); C, 75.45 (75.60); H, 10.00 (9.78); N, 9.26 (8.97).

EXAMPLE 36

2-Isopropyl-3-[1-(2-hydroxypropoxy)-2-methylpropyl]-pyrazolo[1,5-a]pyridine

A solution of 1 g of 2-isopropyl-3-[1-(2,3-epoxypropoxy)-2-methylpropyl]pyrazolo[1,5-a]pyridine (Example 34) in 10 ml of tetrahydrofuran was added to a suspension of 330 mg of lithium aluminum hydride in 10 ml of dry tetrahydrofuran under cooling. The mixture was stirred for 40 minutes, followed by addition of 1 ml of aqueous 15% sodium hydroxide solution with cooling, 3 ml of water and an adequate amount of ether successively. The resulting precipitates were filtered off and the filtrate was extracted with ether. The ether layer was dried over anhydrous sodium sulfate and concentrated to dryness. The residue was recrystallized from hexane to give 840 mg (83%) of the desired product as colorless crystals, mp 112° C.

Analysis (%) for $C_{17}H_{26}N_2O_2$: Calcd. (Found); C, 70.31 (70.53); H, 9.02 (9.07); N, 9.65 (9.65).

EXAMPLE 37

2-Isopropyl-3-methoxymethylpyrazolo[1,5-a]pyridine

To a cold solution of 2.0 g of 2-isopropyl-3-formylpyrazolo[1,5-a]pyridine in 60 ml of methanol were added in small portions 2.0 g of sodium borohydride under cooling and stirring. The mixture was heated to reflux for 2 hours and after cooling, concentrated in vacuo. Water was added to the residue and the mixture was extracted with dichloromethane. The organic layer was dried over anhydrous sodium sulfate and concentrated to give an oily residue, weighing 2.2 g. The residue in 5 ml of dry tetrahydrofuran was added to a suspension of 1.53 g of sodium hydride (55% oil suspension) in 10 ml of dry tetrahydrofuran under stirring and cooling. The mixture was stirred at room temperature for 5 minutes and then at reflux temperature for 15 minutes. After cooled under ice-water, 5.0 g of methyl iodide were added to the mixture. The mixture was stirred at toom temperature for an hour, followed by addition of aqueous 20% ammonium chloride, and extracted with ether. The ether layer was washed with saturated brine, dried over anhydrous sodium sulfate and concentrated to dryness. The residue was subjected to silica gel column chromatography, eluted with dichloromethane, to give 1.2 g (55%) of the desired compound as pale yellow oil.

Analysis (%) for $C_{12}H_{16}N_2O$: Calcd. (Found); C, 70.56 (70.28); H, 7.89 (7.86); N, 13.71 (13.52).

EXAMPLE 38

2-Isopropyl-3-propenylpyrazolo[1,5-a]pyridine

Five grams of 2-isopropyl-3-(1-hydroxypropyl)-pyrazolo[1,5-a]pyridine (Example 8) were dissolved in 50 ml of acetic anhydride. The mixture was heated to reflux for 4 hours and concentrated to dryness. Water was added to the residue. The mixture was brought to alkaline by the addition of potassium carbonate and extracted with dichloromethane. The organic layer was dried over anhydrous sodium sulfate and concentrated to dryness. The residue was subjected to silica gel column chromatography, eluted with ethyl acetate-benzene (1:4) to give 3.6 g of the desired compound as pale yellow oil.

EXAMPLE 39

2-Isopropyl-3-propylpyrazolo[1,5-a]pyridine

A solution of 2.0 g of the compound obtained in Example 38 in 20 ml of ethanol was stirred in a hydrogen atmosphere at atmospheric pressure and room temperature in the presence of 100 mg of 10% palladium-on-charcoal for an hour. The solution was filtered and concentrated to dryness in vacuo. The residue was subjected to silica gel column chromatography, eluted with dichloromethane to give 1.6 g (62%) of the desired compound as colorless needles, mp 41°–42° C.

Analysis (%) for $C_{13}H_{18}N_2$: Calcd. (Found); C, 77.18 (76.61); H, 8.97 (9.04); N, 13.84 (13.60).

Using the procedures described in Example 38 and 39, other new compounds have been obtained, and these physical constants are indicated in Table 5.

TABLE 5

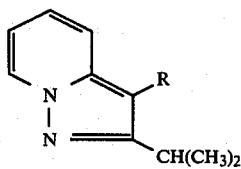

| Example No. | R | M.P. (°C.) | Yield (%) | Anal. (%) Calcd. Found C | H | N |
|---|---|---|---|---|---|---|
| 40 | —CH=C(CH₃)₂ | oil | 75 | 78.46 78.20 | 8.46 8.44 | 13.07 12.99 |
| 41 | CH₂=C—CH(CH₃)₂ | oil | 85 | 78.90 78.86 | 8.83 8.85 | 12.27 12.22 |
| 42 | CHCH₃=C—CH(CH₃)₂ | oil | 54 | 79.29 79.29 | 9.15 9.12 | 11.56 11.52 |
| 43 | —CH₂CH(CH₃)₂ | oil | 89 | 77.73 77.72 | 9.32 9.29 | 12.95 12.89 |
| 44 | CH₃\|—CHCH(CH₃)₂ | oil | 79 | 78.21 77.91 | 9.62 9.61 | 12.16 12.11 |

EXPERIMENT 1

Antagonistic action against SRS-A

The anti-SRS-A action of the compounds of this invention was evaluated using isolated guinea pig ileum. Short segments of guinea pig terminal ileum were suspended in Tyrode solution containing tripelennamine ($3 \times 10^{-7}$ g/ml) and atropine ($3 \times 10^{-7}$ g/ml) and their contractions induced by an addition to the organ bath of 3 U/ml SRS-A* were recorded. The ileum was again contracted after incubation with test compounds for 5 minutes by adding the same amount of SRS-A. The anti-SRS-A action is given in Table 6 as $IC_{50}$ values which indicate the concentration of test compound required to inhibit SRS-A induced ileal contraction by 50%.

*: The SRS-A used in this experiment was prepared from anaphylactic guinea pig lungs. One unit of SRS-A refers to the amount required to produce a contraction of the guinea pig ileum equal in amplitude to that produced by 5 ng histamine base.

TABLE 6

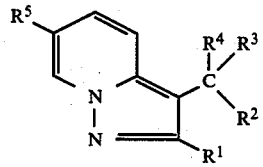

| Example No. | R₁ | R₂ | R₃ | R₄ | R₅ | Antagonistic activity against SRS-A $IC_{50}$ ($\times 10^{-6}$ g/ml) |
|---|---|---|---|---|---|---|
| 5 | —CH(CH₃)₂ | —CH(CH₃)₂ | —H | —OH | —H | 1.75 |
| 6 | " | —cyclopentyl | " | " | " | 10.3 |
| 8 | " | —CH₂CH₃ | " | " | " | 27.0 |
| 9 | " | —CH₂CH₂CH₃ | " | " | " | 26.8 |
| 10 | —CH₃ | —CH(CH₃)₂ | " | " | " | 10.3 |
| 11 | —CH₂CH₂CH₃ | —CH₂CH₂CH₃ | " | " | " | 16.4 |
| 13 | —CH(CH₃)₂ | —CH(CH₃)₂ | " | " | —OCH₃ | 4.9 |
| 15 | " | " | —CH₂CH₃ | " | —H | 1.75 |
| 16 | " | " | —CH₃ | " | " | 23.5 |
| 17 | " | " | —CH₂CH₂CH₃ | " | " | 2.03 |
| 18 | " | " | —CH₂(CH₂)₂CH₃ | " | " | 0.84 |
| 19 | " | " | —CH₂(CH₂)₄CH₃ | " | " | 2.14 |
| 20 | " | " | —CH₂CH=CH₂ | " | " | 1.51 |
| 21 | " | " | —H | —OCH₃ | " | 6.6 |
| 22 | " | " | " | —OCH₂CH₃ | " | 7.2 |
| 23 | " | " | " | —OCH₂CH=CH₂ | " | 1.06 |
| 24 | " | " | " | —OCH₂CH₂CH₃ | " | 5.09 |
| 25 | " | " | " | —OCH₂(CH₂)₂CH₃ | " | 9.98 |
| 26 | " | " | " | —OCH₃ | —CH₃ | 18.4 |
| 27 | " | " | " | —OCH₂CH=CH₂ | " | 3.93 |
| 28 | " | " | " | —OCH₃ | —OCH₃ | 7.36 |
| 29 | " | " | " | —OCH₂CH=CH₂ | " | 3.84 |
| 30 | " | " | —CH₂CH₃ | —OCH₃ | —H | 1.52 |
| 31 | " | " | " | —OCH₂CH=CH₂ | " | 0.27 |
| 32 | " | " | —CH₂CH₂CH₃ | " | " | 0.52 |
| 33 | " | " | —CH₂(CH₂)₂CH₃ | " | " | 2.36 |
| 34 | " | " | —H | —OCH₂CH(O)CH₂ (epoxide) | " | 7.33 |
| 35 | " | " | —CH₂CH₃ | —OCH₂CH₂CH₃ | " | 1.23 |
| 36 | " | " | —H | —OCH₂CH(OH)CH₃ | " | 14.9 |

TABLE 6-continued

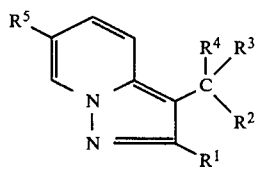

|  |  |  |  |  |  | Antagonistic activity against SRS-A |
|---|---|---|---|---|---|---|
| Example No. | R₁ | R₂ | R₃ | R₄ | R₅ | $IC_{50}$ ($\times 10^{-6}$ g/ml) |
| 37 | " | —H | —H | —OCH₃ | " | 14.7 |
| 39 | " | " | —CH₂CH₃ | —H | " | 2.8 |
| 40 | " | " |  | =C(CH₃)₂ | " | 2.7 |
| 41 | " | —CH(CH₃)₂ |  | =CH₂ | " | 2.45 |
| 42 | " | " |  | =CHCH₃ | " | 0.44 |
| 43 | " | " | —H | —H | " | 2.7 |
| 44 | " | " | —CH₃ | —H | " | 1.6 |

EXPERIMENT 2

Effect on bronchial anaphylactic reaction in vivo

The effect of the compounds of this invention on bronchial anaphylactic reaction in vivo was evaluated using conscious guinea pigs in a condition where SRS-A was preferentially involved in bronchoconstriction (Boot, J. R. et al.: Int. Arch. Allergy Appl. Immunol. 67, 340 (1982)). The guinea pigs which had been sensitized actively with egg albumin 3 to 4 weeks prior were given intraperitoneally with 10 mg/kg diphenhydramine. In these animals, inhaled antigen caused a marked respiratory distress due to bronchoconstriction. The $ED_{75}$ values in Table 7 indicate the oral dose of test compound required to protect 75% of animals from respiratory distress caused by antigen challenge.

From the result given in Table 7, it is confirmed that the compounds of this invention are able to inhibit the SRS-A-induced component of anaphylactic bronchoconstriction at exceedingly low oral doses.

TABLE 7

| Inhibitory activity on bronchial anaphylaxis in conscious guinea pigs | |
|---|---|
| Ex. No. | $ED_{75}$ (mg/kg p.o.) |
| 5 | 0.48 |
| 13 | 0.50 |
| 15 | 0.68 |
| 17 | 0.75 |
| 18 | 0.50 |
| 20 | 0.50 |
| 21 | 0.36 |
| 23 | 0.50 |
| 30 | 1.0 |
| 31 | 0.50 |
| 32 | 2.0 |
| 35 | 0.50 |
| 44 | 0.50 |
| Aminophylline | 3.5 |

What is claimed is:

1. A pyrazolo[1,5-a]pyridine derivative of the formula [I],

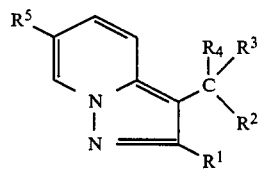

in which $R^1$ is a straight or branched alkyl radical having 1 to 6 carbon atoms, $R^2$ is a hydrogen or straight, branched or cyclic alkyl radical having 1 to 6 carbon atoms, $R^3$ is a hydrogen, straight or branched alkyl having 1 to 6 carbon atoms, or allyl radical $R^4$ is hydrogen, —$OR^6$ (in which $R^6$ is a hydrogen, alkyl having 1 to 5 carbon atoms, which alkyl may optionally be substituted by one or two hydroxy radicals, allyl or 2,3-epoxypropyl radical) or, together with $R^2$ or $R^3$ forms

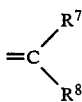

(in which $R^7$ and $R^8$ are each independently a hydrogen or alkyl having 1 to 5 carbon atoms), and $R^5$ is a hydrogen, methyl or methoxy radical, provided that $R^2$, $R^3$, and $R^4$ are not simultaneously hydrogen.

2. A pharmaceutical composition for the treatment of allergic diseases comprising an anti-allergic effective amount of at least one compound according to claim 1 and a pharmaceutically acceptable carrier.

3. A method of treatment for allergic diseases comprising administering an anti-allergic effective amount of at least one compound according to claim 1 to a patient requiring such treatment.

* * * * *